United States Patent [19]

Guzman et al.

[11] Patent Number: 5,024,546
[45] Date of Patent: Jun. 18, 1991

[54] COMPRESSIBLE THREE CHAMBER DEVICE FOR DISPERSING POMADE

[76] Inventors: Julio Guzman, P.O. Box 3495, Ridgewood, N.Y. 11385; George Spector, 233 Broadway Rm. 3815, New York, N.Y. 10007

[21] Appl. No.: 111,293

[22] Filed: Oct. 22, 1987

[51] Int. Cl.⁵ .................... A46B 11/00; A47L 13/12
[52] U.S. Cl. ..................... 401/16; 401/281; 401/25; 401/27; 401/195
[58] Field of Search .......... 401/17, 19, 16, 23, 401/24, 25, 27, 34, 35, 39, 118, 119, 123–125, 129, 137, 195, 281; 132/74.5, 75, 112

[56] References Cited

U.S. PATENT DOCUMENTS

| | | | |
|---|---|---|---|
| 1,368,735 | 2/1921 | Lang | 132/85 |
| 2,097,934 | 11/1937 | Morrison | 132/85 |
| 2,552,708 | 5/1951 | Broneer | 401/39 |
| 3,738,762 | 6/1973 | Moore | 401/17 |
| 4,273,144 | 6/1984 | Morganroth | 132/88.7 |
| 4,277,193 | 7/1981 | Knaus | 401/39 |
| 4,585,018 | 4/1986 | O'Connor | 132/112 |

*Primary Examiner*—Mark L. Bell

[57] ABSTRACT

A pomade externally applied to the skin is provided and consists of soybean oil, peanut oil, wheat germ oil, rose perfume, jasime perfume, hocalito tree leaves, aloe vera and pure rain water. An apparatus for applying the pomade is employed that includes a container that has three chambers. The first chamber is for storing a plurality of cotton balls, the second chamber is for storing and dispensing alcohol and the third chamber is for storing and dispensing the pomade through a brush thereon for application to a person's body.

1 Claim, 1 Drawing Sheet

COMPRESSIBLE THREE CHAMBER DEVICE FOR DISPERSING POMADE

BACKGROUND OF THE INVENTION

The instant invention relates generally to cosmetic preparations and more specifically it relates to a health pomade applicator.

Numerous cosmetic preparations have been provided in prior art that are adapted to be applied to the skin and scalp of a person. For example, U.S. Pat. Nos. 3,839,553; 3,879,534 and 4,459,285 all are illustrative of such prior art. While these units may be suitable for the particular purpose to which they address, they would not be as suitable for the purposes of the present invention as heretofore described. A prior application Ser. No. 767,916 filed 8-21-85 was abandoned 3-2-87 in which the following references were cited: U.S. Pat. Nos. 1,368,735; 2,097,934; 3,738,782; 3,839,553; 3,879,534; 4,273,144; 4,459,285; 4,474,763; 4,505,902; 4,511,555; 4,552,755; and 4,585,018.

SUMMARY OF THE INVENTION

A primary object of the present invention is to provide a health pomade applicator that will overcome the shortcomings of the prior art devices.

Another object is to provide a health pomade applicator that will store the proper ingredients used in preparing the pomade so that the pomade can be dispensed therefrom.

An additional object is to provide a health pomade applicator that includes a built in brush so that the pomade can be applied directly to the various parts of the body for treatment.

A further object is to provide a health pomade applicator that is simple and easy to use.

A still further object is to provide a health pomade applicator that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
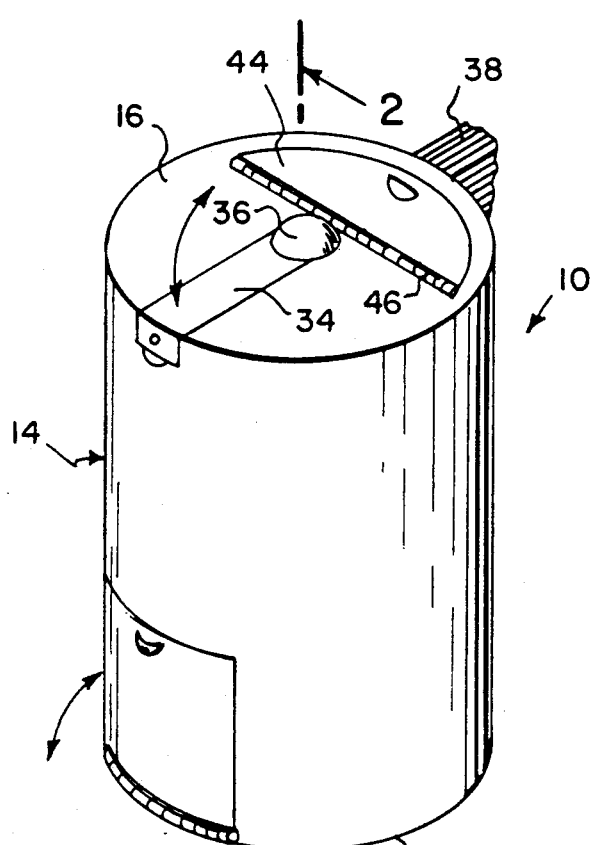
FIG. 1 is a perspective view of the invention.
Figure 2:
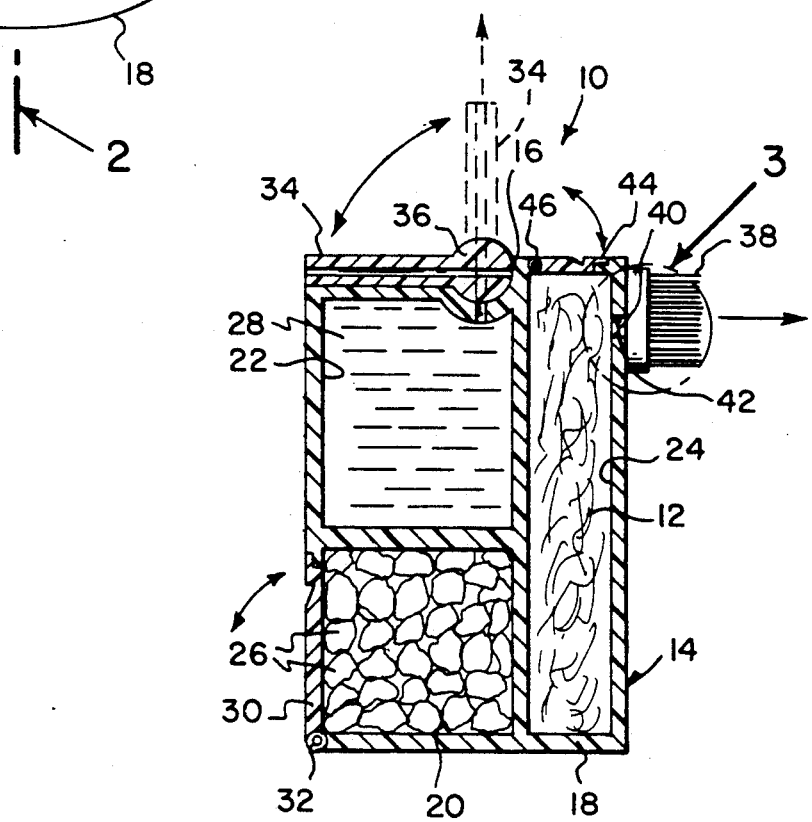
FIG. 2 is a cross sectional view taken along line 2—2 in FIG. 1 showing the various compartments within.

Turning now descriptively to the drawings, in which similar reference characters denote similar elements throughout the several views, FIGS. 1 and 2 illustrate a device 10 for dispensing pomade 12, consisting of a compressible container 14 having a cover 16, a bottom 18 and three chambers 20, 22 and 24 wherein a first chamber 20 is over the bottom 18 storing a plurality of cotton balls 26, a compressible second chamber 22 is under the cover 16 for storing alcohol 28 and a compressible third chamber 24 extends from the cover 16 to the bottom 18 adjacent to the first and second chambers 20 and 22. A door 30 is hinged at 32 to the first chamber 20 so that when the door is opened the cotton balls 26 can be removed. A pivot spout 34 is mounted on the cover 16 and is fluidly connected to the second chamber 22. The spout 34 is pivotable at ball socket 36 to a raised open position communicating with the second chamber 22. A brush 38 with a one way check valve 40 is fluidly connected via conduit 42 to the third chamber 24 so that when the third chamber is compressed pomade 12 will exit to mix within the brush 38 for application to a persons body (not shown).

Figure 3:
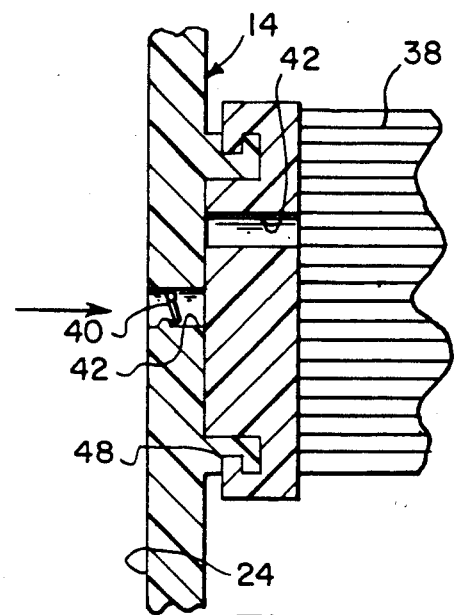
FIG. 3 is an enlarged cross sectional view as indicated by arrow 3 in FIG. 2 showing the rotatable brush in greater detail for dispensing the pomade therefrom.

A second door 44 is hinged at 46 on the cover 16 over the third chamber 24 so that when the second door 44 is opened the pomade 12 can be filled therein. As best seen in FIG. 3, the container 14 has an annular track 48 formed thereon in cooperation with the brush 38, making the brush rotatable. The brush 38 can be turned in one instance to a position to be fluidly connected to the third chamber 24 and in another instance to another position not to be fluidly connected to the third chamber 24.

The pomade 12 is externally applied to the skin and consists of soybean oil, peanut oil, wheat germ oil, rose perfume, jasmine perfume, hocalito tree leaves, aloe vera and pure rain water in the following proportions:

| | |
|---|---|
| Soybean Oil | 2¼ oz. |
| Peanut Oil | 1 oz. |
| Wheat Germ Oil | ½ oz. |
| Rose Perfume | 1/16 oz. |
| Jasmine Perfume | 1/16 oz. |
| Freshly Ground Leaves Of A Tropical Tree Called Hocalito | ½ oz. |
| Freshly Ground Aloe Vera | ½ oz. |
| Pure Rain Water | ¼ oz. |

The pomade 12 can treat the following ailments:
1. Fingernails and the adjoining skin near the nails.
2. Toenails and the adjoining skin near the nails.
3. Warts on the face and on various other parts of the body.
4. Leg veins, varicose veins, and poor circulation in the legs.
5. Dry skin.
6. Dandruff and loss of hair.
7. Alleviates arthritis.

APPLICATION OF THE POMADE

1. For fingernails

First a cotton ball 26 with alcohol 28 is applied once on the nails. Afterwards, a quarter of a teaspoon of the pomade 12 is applied and rubbed on the nails, and hands for three minutes. Then a moist cotton ball 26 with alcohol 28 is reapplied. Then another quarter of a teaspoon of pomade 12 is reapplied and rubbed or massaged on nails and hands for three minutes. This is done three times a day. It is convenient in the morning and before going to bed.

2. for toenails

The feet are washed in warm water. Afterwards a cotton ball 26 with alcohol 28 is applied, by hand, both on the toenails and the entire foot, especially on the soles. If the ailment is on one foot, the treatment is applied on both feet. Afterwards, a half of a teaspoon of pomade 12, is rubbed onto the affected area for five minutes. Finally a moist cotton ball 26 with alcohol 28 is used to remove the pomade 12. This is done three times a day.

3. Warts on the face and other parts of the body

First, water is boiled and cooled until the water is almost cold. Then, affected areas are washed. A cotton ball 26 with alcohol 28 is applied on the warts. Afterwards apply a small amount of the pomade 12 onto the affected area for two minutes. Then, reapply a moist cotton ball 26 with alcohol 28 to remove the pomade 12. This is done three times a day. This should be done gently since affected areas are different from the feet. This treatment must be done continually, day after day, without fail.

4. Varicose veins and poor circulation

First, water is boiled to destroy the chlorine content. Afterwards, when the water is cold, wash the affected part of the leg. Then, a moist cotton ball 26 with alcohol 28 is applied onto the affected area. Take a full teaspoon of pomade 12 and apply onto the affected area for five minutes. Then, reapply a moist cotton ball 26 with alcohol 28. Then, take one quarter of a teaspoon of the pomade 12 and apply it onto the affected area for one minute. This is done three times a day. One should place a pillow beneath the legs and feet during the treatment period.

5. Dry skin or eczema

Boil water to destroy the chlorine content. When the water is almost cold, the affected area is bathed. The affected area should be dried preferably with a sterilized towel. Then, a moist cotton ball 26 with alcohol 28 is applied. A full teaspoon of the pomade 12 is applied onto the affected area of the skin until the pomade is used up. Then, a moist cotton ball 26 with alcohol 28 is applied onto the affected area. This is done three times a day. While this treatment is in effect, a person should not use soap or detergent. Every time one bathes, one should boil the water and use the water when it is lukewarm. The treatment should be accomplished immediately after drying the skin with a sterilized towel.

6. The scalp and dandruff

For people whose hair is falling out, the pomade can stop hair loss. Before using a shampoo, one should apply a quarter of a teaspoon of pomade 12 and apply or message to the scalp for three minutes. The shampoo should be purshaded at the health store and it should not contain preservatives or chemicals. The shampoo should be natural. If this treatment is followed as per instructions, dandruff will disappear.

7. Arthritis

The pomade 12 can be helpful if applied and rubbed onto affected areas four times a day. Exercise must be continual and frequent. One should massage for two minutes and rest for three minutes. Do this every three minutes for twenty minutes in the morning and before going to bed, at least two times a day.

One should not expect results overnight. It can take up to six months to achieve lasting results. Not all people respond in the same manner. The pomade 12 is rich in vitamins for the skin and nails.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A device for dispensing pomade comprising a compressible container having a cover, a bottom and three chambers, wherein a first chamber is over the bottom storing a plurality of cotton balls, a compressible second chamber is under the cover for storing alcohol and a compressible third chamber extends from said cover to said bottom adjacent to said first and second chambers further comprising:
    (a) a door hinged to said first chamber so that when said door is opened said cotton balls can be removed;
    (b) a pivot spout mounted on said cover and fluidly connected to said second chamber said spout being pivotable to a raised open position communicating with said second chamber;
    (c) a brush with a one way check valve fluidly connected to said third chamber so that when said third chamber is compressed pomade will exit to mix within said brush for application to said person's body;
    (d) a second door hinged on said cover over said third chamber so that when said second door is opened said pomade can be filled therein; and
    (e) said container having an annular track formed thereon in cooperation with said brush, making said brush rotatable, having means whereby said brush can be turned in one instance to a position to be fluidly connected to said third chamber and in another instance to another position not to be fluidly connected to said third chamber.

* * * * *